US011287930B2

(12) United States Patent
Moller et al.

(10) Patent No.: US 11,287,930 B2
(45) Date of Patent: *Mar. 29, 2022

(54) CAPACITIVE SENSORS FOR DETERMINING EYE GAZE DIRECTION

(71) Applicant: Microsoft Technology Licensing, LLC, Redmond, WA (US)

(72) Inventors: Christian Moller, Redmond, WA (US); Flavio Protasio Ribeiro, Bellevue, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 1031 days.

This patent is subject to a terminal disclaimer.

(21) Appl. No.: 15/848,797

(22) Filed: Dec. 20, 2017

(65) Prior Publication Data

US 2018/0125358 A1 May 10, 2018

Related U.S. Application Data

(63) Continuation of application No. 14/729,524, filed on Jun. 3, 2015, now Pat. No. 9,888,843.

(51) Int. Cl.
*G06F 3/044* (2006.01)
*G06F 3/01* (2006.01)
(Continued)

(52) U.S. Cl.
CPC ............ *G06F 3/044* (2013.01); *A61B 3/0025* (2013.01); *A61B 3/113* (2013.01); *G06F 1/1686* (2013.01); *G06F 1/1698* (2013.01); *G06F 3/013* (2013.01)

(58) Field of Classification Search
CPC ....... A61B 3/113; A61B 3/0025; A61B 5/163; G06F 1/1686; G06F 3/013; G06F 3/044; G06F 3/0446; G06F 3/0448
(Continued)

(56) References Cited

U.S. PATENT DOCUMENTS 6,307,384 B2   10/2001  Havey et al.
8,115,753 B2   2/2012   Newton
(Continued)

FOREIGN PATENT DOCUMENTS

CN    201402457      2/2010
CN    102906623 A    1/2013
(Continued)

OTHER PUBLICATIONS

"First Office Action and Search Report Issued in Chinese Patent Application No. 201680032446.X", dated Nov. 22, 2019, 18 Pages.
(Continued)

*Primary Examiner* — Travis S Fissel
(74) *Attorney, Agent, or Firm* — Ray Quinney & Nebeker P.C.; John O. Carpenter (57) ABSTRACT

An apparatus for tracking eye gaze includes a capacitive sensor array having a plurality of capacitive sensors. The capacitive sensor array is configured to detect eye movement based at least on a proximity of the plurality of capacitive sensors to a part of an eye of a user (e.g., a bulge in the cornea). A frame of the apparatus is configured to be worn on a head of the user and configured to support the capacitive sensor array positioned in front of the eye. A control circuit of the apparatus is configured to receive signals from the capacitive sensor array. A body electrode of the apparatus is positioned on the frame and electrically connected to the control circuit, the body electrode configured to establish an electrical connection with a body of the user. A conductive line of the apparatus connects the body electrode to the control circuit.

20 Claims, 7 Drawing Sheets

(51) Int. Cl.
  *A61B 3/00* (2006.01)
  *A61B 3/113* (2006.01)
  *G06F 1/16* (2006.01)
(58) Field of Classification Search
  USPC .......................................................... 351/209
  See application file for complete search history.

(56) References Cited

U.S. PATENT DOCUMENTS

| | | | |
|---|---|---|---|
| 8,398,239 B2* | 3/2013 | Horning | G06K 9/00604 351/209 |
| 8,477,425 B2 | 7/2013 | Border et al. | |
| 8,510,166 B2 | 8/2013 | Neven | |
| 8,864,305 B2 | 10/2014 | Pletcher et al. | |
| 8,870,370 B1 | 10/2014 | Otis et al. | |
| 8,933,907 B2 | 1/2015 | Hanauer et al. | |
| 2004/0059212 A1* | 3/2004 | Abreu | A61B 5/02055 600/373 |
| 2004/0070729 A1* | 4/2004 | Wiebe | G06F 3/012 351/209 |
| 2006/0061544 A1 | 3/2006 | Min et al. | |
| 2009/0262973 A1 | 10/2009 | Koshizen et al. | |
| 2011/0095771 A1* | 4/2011 | Reime | G01V 3/088 324/686 |
| 2012/0147328 A1 | 6/2012 | Yahav | |
| 2012/0212398 A1 | 8/2012 | Border et al. | |
| 2012/0235885 A1* | 9/2012 | Miller | G06F 3/011 345/8 |
| 2012/0235886 A1 | 9/2012 | Border et al. | |
| 2012/0281181 A1 | 11/2012 | Chen et al. | |
| 2013/0016065 A1* | 1/2013 | Reynolds | G06F 3/047 345/174 |
| 2013/0091437 A1 | 4/2013 | Ludwig | |
| 2013/0215147 A1 | 8/2013 | Hilkes et al. | |
| 2014/0098226 A1 | 4/2014 | Pletcher et al. | |
| 2014/0104376 A1* | 4/2014 | Chen | G08B 13/19643 348/36 |
| 2014/0160424 A1 | 6/2014 | Benko et al. | |
| 2014/0240655 A1 | 8/2014 | Pugh et al. | |
| 2014/0296672 A1 | 10/2014 | Etzkorn | |
| 2015/0015847 A1 | 1/2015 | Bergman et al. | |
| 2015/0061999 A1* | 3/2015 | Kim | G06F 3/013 345/156 |
| 2015/0070470 A1* | 3/2015 | McMURROUGH | G06K 9/6211 348/46 |
| 2015/0091859 A1* | 4/2015 | Rosenberg | G06F 3/044 345/174 |
| 2015/0296135 A1* | 10/2015 | Wacquant | G06K 9/00261 348/207.11 |

FOREIGN PATENT DOCUMENTS

| | | | |
|---|---|---|---|
| CN | 103649874 A | 3/2014 | |
| CN | 104066371 A | 9/2014 | |
| EP | 1542363 A1 | 6/2005 | |
| EP | 2806782 A1 * | 12/2014 | ............. A61B 3/113 |
| WO | 9113584 | 9/1991 | |
| WO | 2013110846 | 8/2013 | |

OTHER PUBLICATIONS

"Final Office Action Issued in U.S. Appl. No. 14/729,524", dated Dec. 30, 2016, 16 Pages.

"Non Final Office Action Issued in U.S. Appl. No. 14/729,524", dated Jul. 5, 2016, 16 Pages.

"Second Office Action Issued in Chinese Patent Application No. 201680032446.X", dated Jun. 9, 2020, 19 Pages.

"International Preliminary Reporton Patentability Issued in PCT Application No. PCT/US2016/031698", dated Jul. 4, 2017, 11 Pages.

"International Search Repod and Written Opinion Issued in PCT Application No. PCT/US2016/031698", dated Jul. 28, 2016, 15 Pages.

"Wearable Glass from Nokia Gets More Force with One of Recent Patents About 'Capacitive Eye Tracking Sensor'", NPU, Sep. 7, 2013, 11 pages, http://www.nokiapoweruser.com/wearable-glass-from-nokia-gets-more-force-with-one-of-recent-patents-about-capacitive-eye-tracking-sensor/.

"Written Opinion of the International Preliminary Examining Authority Issued in PCT Application No. PCT/US2016/031698", dated Apr. 13, 2017, 10 Pages.

Cheng et al., "Active Capacitive Sensing: Exploring a New Wearable Sensing Modality for Activity Recognition", In Proceedings of 8th International Conference on Pervasive Computing, May 17, 2010, 7 pages.

Jack Purcher, "Microsoft Invents Eyewear with Multi-Touch Interactive Sensors", Jun. 17, 2014, 7 pages, Available at:http://www.patentlymobile.com/2014/06/microsoft-invents-eyewear-with-multi-touch-interactive-sensors.html.

Natasha Steinhausen et al., "A Three Sensor Eye Tracking System Based on Electrooculography", In Proceedings of IEEE Sensors, Nov. 2, 2014, 4 pages.

"Third Office Action Issued in Chinese Patent Application No. 201680032446.X", dated Sep. 16, 2020, 7 Pages.

* cited by examiner

CAPACITIVE SENSORS FOR DETERMINING EYE GAZE DIRECTION

CROSS-REFERENCE TO RELATED APPLICATIONS

This application is a continuation of U.S. patent application Ser. No. 14/729,524, filed Jun. 3, 2015, which is hereby incorporated by reference in its entirety.

BACKGROUND

Eye gaze tracking technology has been used in several different fields including human-computer interface for assisting a disabled person interact with a computer. For instance, an eye gaze tracker may be used as a mouse emulator for a personal computer, helping a disabled person move a cursor on a display screen to control their environment and communicate messages with their eyes. Gaze tracking has also been used for industrial control, aviation, and emergency room situations where both hands are needed for tasks other than operation of a computer.

Eye gaze tracking systems have used cameras positioned on a wearable headgear frame to measure eye movement/position. Through such monitoring of eye movement, the camera may assist in determining the point of gaze of the eye of the wearer. Use of a camera to monitor eye movement and position may be problematic due to the cost and complexity of the camera equipment, high power requirements for the camera, and the bulk or obtrusiveness of a camera mounted on the headgear.

SUMMARY

Gaze tracking techniques and mechanisms are described herein. In one or more embodiments, the wearable device includes a lens; a plurality of sensors positioned on a surface of the lens or within the lens, wherein each sensor of the plurality of sensors is positioned in a separate location and is electrically disconnected from each additional sensor on the surface of the lens or within the lens, and wherein the plurality of sensors is configured to detect eye movement based at least on a proximity of the plurality of sensors to a part of an eye of a user; and a frame configured to be worn on a head of the user, wherein the frame supports the lens and the plurality of sensors.

In another embodiment, an apparatus for eye gaze tracking includes a plurality of sensors positioned on a surface of a lens or within the lens, wherein each sensor of the plurality of sensors is positioned in a separate location and is electrically disconnected from each additional sensor on the surface of the lens or within the lens. The apparatus further includes at least one processor configured to: receive signals from the plurality of sensors positioned in front of an eye of a user; determine a plurality of measured capacitances from the received signals; and ascertain an eye gaze direction of the eye of the user based at least on the plurality of measured capacitances.

In another embodiment, a method is provided for identifying eye gaze direction. The method includes receiving, using a processor, signals from a plurality of sensors positioned on a surface of at least one lens or within the at least one lens, wherein each sensor of the plurality of sensors is positioned in a separate location and is electrically disconnected from each additional sensor on the surface of the lens or within the lens, and wherein the at least one lens is supported on a frame of a headgear apparatus positioned in front of a right eye and a left eye of a user; determining measured capacitances from the received signals for the right eye and the left eye; and ascertaining eye gaze direction based at least on the measured capacitances.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DESCRIPTION OF THE DRAWING FIGURES

For a more complete understanding of the disclosure, reference is made to the following detailed description and accompanying drawing figures, in which like reference numerals may be used to identify like elements in the figures.

While the disclosed systems and methods are representative of embodiments in various forms, specific embodiments are illustrated in the drawing (and are hereafter described), with the understanding that the disclosure is intended to be illustrative, and is not intended to limit the claim scope to the specific embodiments described and illustrated herein.

DETAILED DESCRIPTION

Disclosed herein are apparatuses, systems, and methods for tracking eye gaze direction with respect to the user's orientation. Unlike eye gaze tracking systems fixed in space (e.g., systems fixed to a wall or within a computer oriented in a direction toward the person being monitored), the eye gaze tracking methodology disclosed herein is from the user's head's frame of reference. For example, if a user turns his or her head, the user's eye gaze direction does not necessarily change (e.g., the user could remain looking straight ahead, just from a different frame of reference). In other words, a user's eye gaze direction is monitored by an apparatus attached to the user's head that moves with the user. Such an eye gaze tracking apparatus, system, or method has several potential end-uses or applications, including any application where tracking eye gaze from the user's frame of reference is desired. This may include virtual reality or augmented realty systems and devices. Personal gaming systems and devices also may be applicable end uses.

Eye gaze tracking from a user's frame of reference may be implemented using capacitive sensors positioned in front of a user's eyes in a head-mounted device or system (e.g., wearable glasses). The capacitive sensor may comprise one or more electrodes forming a capacitor. Such a capacitive sensor system may provide an inexpensive, reliable, and unobtrusive alternative to using a camera to monitor eye movement. Capacitive sensors may be able to track eye movement in the dark, unlike some cameras. Additionally, capacitive sensors may be less expensive than camera equipment (as the capacitive sensor arrangement may not include optical components). Furthermore, signal processing from the capacitive sensors may be easier and/or faster (i.e., lower latency) than signal processing from a camera. This may allow for reduced power consumption (e.g., 100 times less power), and thus a smaller power source affixed to the headgear, when compared with camera equipment. Cameras and their larger battery requirements add bulk or obtrusiveness to the headgear as well.

Eye gaze tracking using capacitive sensors is based at least on the specific shape of the eye. Specifically, the cornea of an eye bulges or extends from the eye socket and otherwise spherical shape of the eye. The direction of a user's gaze may be determined based at least on the proximity of the bulge in the cornea to the capacitive sensor positioned in front of the eye. Such an eye tracking system using capacitive sensors may therefore be configured to each individual user based at least on universal aspects of all potential users or individual aspects of the shapes of a user's eyes. In other words, in certain examples, a capacitive sensor eye tracking device or system may be implemented to be operator friendly with minimal configuration or initial setup. In other examples, a capacitive sensor eye tracking device or system may be implemented to be specifically configured to an individual user through an initial configuration wherein the system identifies characteristics of the specific user's eyes and gaze directions.

Capacitive Sensor Gaze Tracking Apparatuses and Systems

Figure 1A:
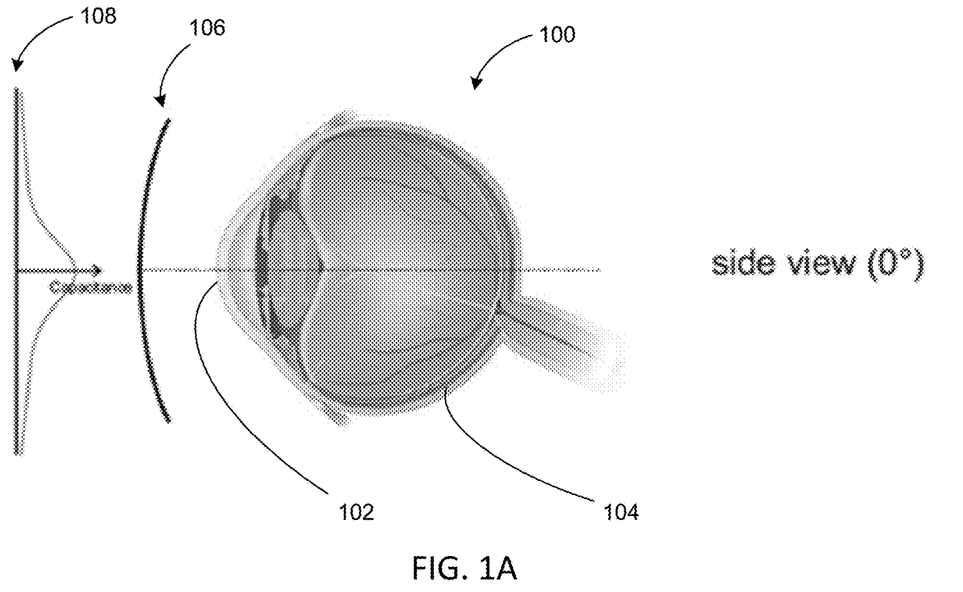
FIGS. 1A and 1B depict side-views of an eye positioned in front of a sensor element in accordance with one example.
Figure 1B:
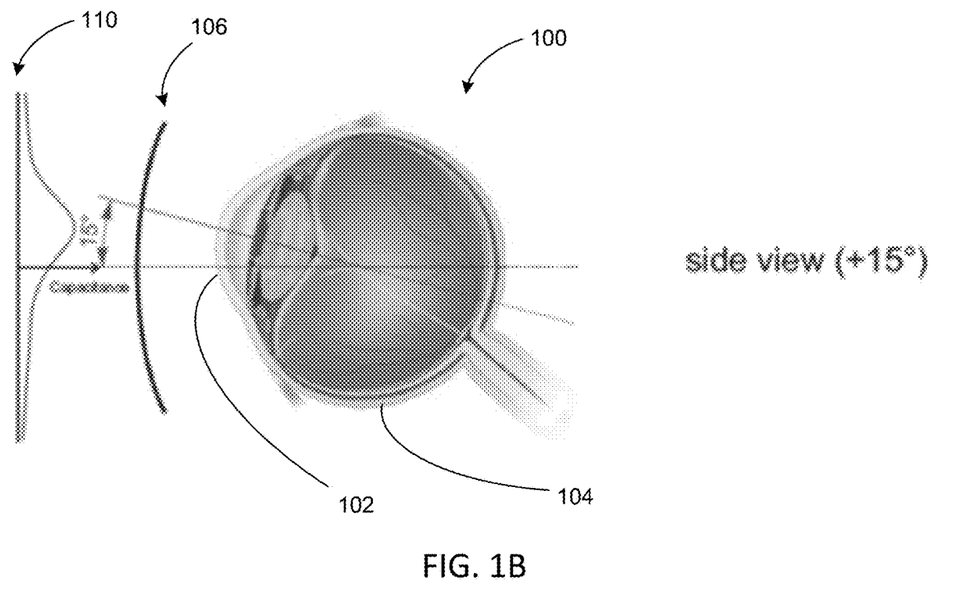

FIGS. 1A and 1B depict side-views of an eye positioned in front of a capacitive sensor. As depicted, the eye 100 includes a cornea 102 positioned in a front portion of the eye 100 covering the iris, pupil, and anterior chamber. The cornea 102 borders with the sclera 104 or white of the eye. Additionally, the cornea 102 bulges or extends from the spherical shape of the sclera 104. Due to the non-spherical nature of the eye at the cornea 102, eye movement or gaze tracking may be determined using capacitive sensors by tracking the cornea 102.

As depicted in FIGS. 1A and 1B, a grid or array of capacitive sensors 106 is positioned, (e.g., on a lens supported by a frame), in front of the eye 100. Due to the bulge in the cornea 102 of the eye 100, the cornea 102 may be the closest to one or more capacitance sensors in the array of sensors 106. Measured capacitance at the various sensors in the array may be plotted on a curve 108 (depicted here in two-dimensions for simplicity). In curve 108, the vertical axis of the curve 108 represents the vertical position across the array of capacitance sensors 106, and the horizontal axis represents the capacitance measured at a sensor corresponding with the position on the vertical axis. As such, the direction of the eye gaze correlates with the largest measured capacitance (e.g., on the order of magnitude of a femtofarad or a fraction of a picofarad). For example, in FIG. 1A, the eye 100 is gazing straight forward, parallel to the ground (defined as a 0° angle), and the measured capacitance curve 108 has a peak or highest measurement at a sensor element positioned at this viewing angle. When the eye gazes upward at a 15° angle, as depicted in FIG. 1B, the measured capacitance curve 110 shifts as well. The cornea 102 is now located closer to a sensor element positioned higher within the grid of sensors 106.

In certain examples, a contact lens may be placed over the cornea 102 of the eye 100 to assist in monitoring eye gaze movement. The contact lens may be made with or embedded with a conductive material that may be detected by the array of capacitance sensors 106. In certain examples, the conductive material within the contact lens is positioned within the circumference of the cornea. In alternative examples, the conductive material within the contact lens is positioned around the circumference of the cornea.

Movement of the eyelid of the eye may influence determination of the eye gaze direction. For instance, when the eyelid closes, the eyelid covers the cornea 102 and becomes closer to the capacitance sensors 106. Various locations along the array of sensors 106 may detect an increase in the measured capacitance. Therefore, in certain examples, based at least on the change in measured capacitance, or the overall profile of the measured capacitance, it is possible to identify if the user's eyes are open or closed. In certain processing applications, the blinking of the eye may be recognized but purposefully rejected by the processor as a false reading of the actual eye gaze direction. In other processing applications, if a user's eye lid is closed for an extended period of time, the processor may acknowledge that the eye is not blinking but is closed. This may be beneficial in various scenarios where it is important to identify if a person is alert or in danger of falling asleep. For example, monitoring eye gaze and eyelid movement (e.g., closure of the eyelid for a prolonged period of time) may be useful for the operator of a vehicle (e.g., truck, car, train, plane).

Capacitive sensors may be placed on or within a transparent, semi-transparent, or opaque substrate supported by a frame or headgear configured to be worn on the head of a user. The frame may be an eyeglass frame supporting right and left eye lenses. Alternatively, the frame may support a single lens or viewing area positioned in front of one or both eyes. In yet other examples, the frame may support a plurality of viewing areas positioned in front of one or both eyes of the user.

Figure 2:
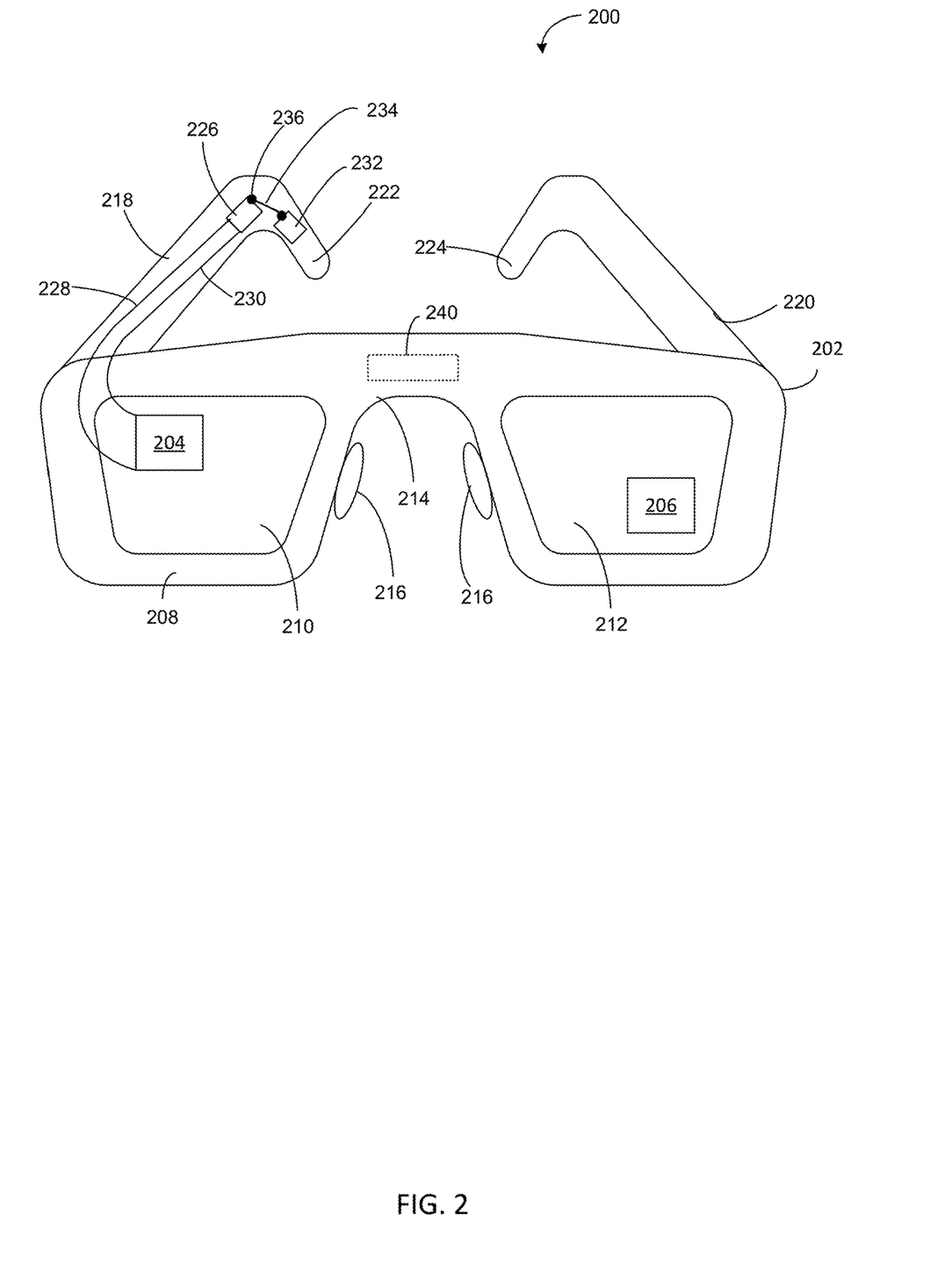
FIG. 2 depicts an example of a frame supporting a plurality of sensors.

FIG. 2 depicts a non-limiting example of an apparatus 200 having a frame 202 supporting capacitive sensors 204, 206. The frame 202 includes a frame front 208 having two viewing areas 210, 212 for the right and left eyes, respectively. The frame 202 also includes a bridge 214 configured to be positioned over the nose of the user. The bridge 214 may include nose rests or pads 216 configured to support the weight of the frame on the user's nose. The frame 202 may include at least one end piece 218, 220 configured to extend from the frame front 208 and rest over an ear of the user. The end piece 218, 220 may include a temple 222, 224 that extends over and/or behind the ear of the user to help hold the frame 202 in place.

At least one capacitive sensor 204 is positioned within the viewing area for the right eye 210. Additionally, at least one capacitive sensor 206 is positioned within the viewing area for the left eye 212. As depicted in FIG. 2, at least one of the capacitive sensors 204 is in communication with a control circuit or analog front-end circuit 226. The control circuit 226 may be secured on or within the frame 202 of the apparatus 200. As depicted, the control circuit 226 is positioned on or within an end piece 218 of the frame 202. (Alternatively, the control circuit may be positioned on or within the frame front or bridge of the frame.)

The control circuit 226 is configured to provide power to and receive signals from the capacitive sensor 204. This may be accomplished through one or more connection or bus lines 228, 230 between the control circuit 226 and the sensor 204. For example, a connection or bus line may be provided to connect the capacitive sensor to an amplifier circuit within the control circuit. Additionally, a connection or bus line may be provided to connect the capacitive sensor to a voltage source within the control circuit.

The control circuit 226 may be configured to provide measured capacitance readings to a computing device for further analysis. For example, the control circuit 226 may be in communication with an analog-digital converter (ADC), firmware, and/or a processor and memory associated with a computing device. The ADC, firmware, processor, and memory may be positioned on or within the frame of the apparatus. Alternatively, ADC, firmware, processor, and/or memory may be remotely or externally connected to the control circuit. Remote connections include wired and/or wireless connections. The wired connection may comply with a standard such as inter-integrated (I2C) protocol, serial peripheral interface (SPI), universal serial bus (USB), or IEEE-1394. The wireless connection may comply with a standard such as Bluetooth, IEEE 802.11 (wireless LAN), ultra-wide band (UWB) radio link, or infrared data association (IrDA) link.

As depicted in FIG. 2, the apparatus 200 also includes a body electrode 232 positioned on or within the frame 202. The body electrode 232 may be electrically connected to the control circuit 226. The body electrode 232 may be any conductive material that may provide good conduction between the user and frame, such as copper, silver, or aluminum. A conductive line 234 may be provided on or within the frame 202 of the apparatus 200, wherein the conductive line 234 connects the body electrode 232 to the control circuit 226. In certain examples, a conductive line may also connect the control circuit 226 with the capacitive sensor 204. The conductive line 234 may be made of a similar or different conductive material as the body electrode 232 (e.g., copper, silver, or aluminum wire). In certain examples, as depicted in FIG. 2, the conductive line 234 connects at a ground node 236 in the control circuit 226. Through such an arrangement, the body electrode 232 may be configured to establish an electrical connection with the body (e.g., head) of the user. The electrical connection provides a grounding connection between the apparatus 200 and the earth through the body. As such, the body electrode 232 may assist in increasing capacitance measurement dynamic range, reducing variations due to movement of the apparatus 200 with respect to the body of the user, and reducing undesired capacitance noise. Because the change in measured capacitance is on the order of magnitude of a femtofarad or fraction of a picofarad, any reduction in noise may improve the ability to track eye gaze through the capacitance sensors.

The body electrode 232 may be positioned on the frame 202 at a location that provides a point of contact with the user's body. The position of the body electrode 232 on the frame may be optimized such that the body electrode 232 provides high contact conduction and/or low contact resistance to the user. For example, as depicted in FIG. 2, the body electrode 232 is positioned on the temple 224 of the frame 202, wherein the electrical connection is made at a location behind the ear of the user. Alternatively, the body electrode 232 may be positioned on the bridge 214 of the frame 202 (e.g., at the nose rest or pad 216). As noted, the position of the body electrode 232 on or within the pad 216 may be optimized to provide high contact conduction and/or low contact resistance to the user's nose.

In certain examples, a camera 240 (e.g., a video camera) may be positioned on the frame 202 of the apparatus 200. The camera 240 may be a frame of reference camera configured to capture real time images positioned in front of the user wearing the apparatus. Like the control circuit 226, the camera 240 may be in communication with a processor or memory associated with a computing device. Such a processor or memory may be positioned on or within the frame 202 of the apparatus 200. Alternatively, the processor and/or memory may be remotely or externally connected to the camera 240. Remote connections include wired and/or wireless connections, such as those discussed above with the control circuit.

The camera 240 may be useful to determine at what object or location the user is looking. In one example, the capacitive sensors may detect that the eyes are gazing up and to the right. At the same time, the camera has captured an image including the direction of the user's gaze. Based on the user's gaze, and the objects within the captured image, the apparatus and a connected processor may assist in identifying an object positioned in the upper right corner of the image that matches with the direction of the user's gaze. For instance, the user could be grocery shopping, and the user's eyes could move up and to the right to see an item on sale within the shopping aisle. Based on this identification, the eye gaze detection could lead to an interaction with the user, such as notifying the user about an interest in making a purchase of the item identified.

Figure 3:
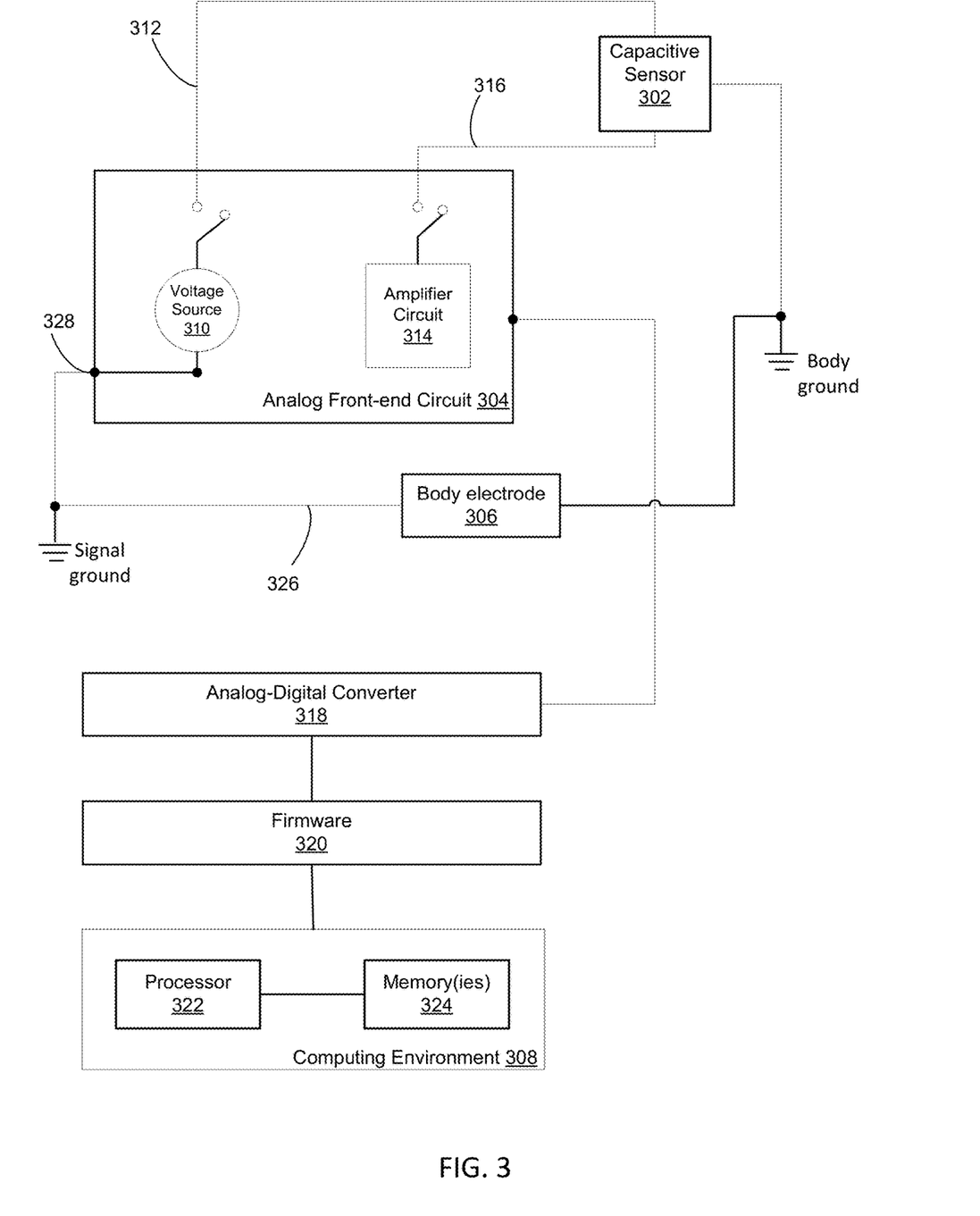
FIG. 3 depicts an example of a block diagram of a computing environment including a capacitive sensor connected, a control circuit, and a body electrode.

FIG. 3 depicts an example of a block diagram of a capacitive sensor 302 in communication with a control circuit or analog front-end circuit 304, body electrode 306, and computing environment 308. The analog front-end circuit 304 includes a voltage source 310 to provide power to the capacitive sensor 302 via a connection line or bus line 312. The analog front-end circuit 304 also includes an amplifier circuit 314 to receive signals from the capacitive sensor via an additional connection line or bus line 316. The analog front-end circuit 304 is configured to amplify the received signals and provide the amplified signals to the computing environment 308 for further analysis.

As depicted in FIG. 3, a body electrode 306 is electrically connected to the analog front-end circuit 304. A conductive line 326 connects the body electrode 306 at the analog front-end circuit 304. Specifically, the conductive line 326 connects a ground node 328 in the analog front-end circuit 304 with the body electrode 306. The arrangement provides two ground nodes (a signal ground and a body ground). The signal ground is connected to the analog front-end circuit 304, and the body ground is the human body. As described herein, the body electrode 306 assists in bringing the potentials of the signal and body grounds as close as possible.

As depicted in FIG. 3, the analog front-end circuit 304 is in communication with an analog-digital converter (ADC) 318. The ADC 318 may be a part of the analog front-end circuit 304 or the computing environment 308. The ADC 318 is connected with firmware 320, which in turn is connected with the computing environment 308. In certain examples, the firmware 320 is part of the computing environment 308. The computing environment 308 may include one or more processors 322 or memories 324, among other components. (Further discussion regarding an example of a computing environment is provided below with discussion of FIG. 7.)

The one or more processors 322 of the computing environment 308 may be configured to analyze the measured capacitance data through one or more algorithms or computer program codes designed to determine eye gaze direction. In certain examples, the processor 322 determines a measured capacitance by calculating the average capacitance over a number of cycles or measurements.

In certain examples, the capacitance data is measured by the sensor 302 and processed by the processor 322 in 100 milliseconds (ms) or less. In other words, the direction of the eye gaze may be determined within 100 ms. In other examples, the capacitance may be measured and processed in 50 ms, 20 ms, 10 ms, or 1 ms or less. Such a low latency in response time provides an ability to track and process eye gaze contemporaneously with the user's potentially rapid eye movements.

Computer program code may be designed with the processor 322 to calibrate the capacitance sensors to the shape of the apparatus frame and/or the shape of the user's head. The user's eyes, the frame, and the viewing area(s) of the frame, are all not two-dimensional. The user's head and positioning of the eyes are not uniform from user to user. The frame may curve around the user's head. Capacitive sensors affixed to the surface, or embedded within the viewing area(s) of the frame may follow the curves of the viewing area(s). A calibration of the sensors based at least on the user's head and the shape of the frame of the apparatus may be provided for improved eye gaze tracking.

In some examples, computer program code may be designed with the processor 322 to calibrate the apparatus to an individual user's eye. This may include conducting several initial tests with the user, wherein the user is directed to look in certain directions. Baseline eye gaze capacitance measurements may be determined for the user. In other examples, the computer program code may be designed to calibrate the apparatus for multiple potential users. This calibration may include conducting several initial tests with several users to develop a calibration table or baseline capacitance measurements that may be used by most users without additional setup or calibration. In other words, a new user may be able to put on and begin using the headgear apparatus with minimal or no setup.

Computer program code may also, or alternatively, be designed with the processor 322 to identify and adjust eye gaze direction calculations based at least on changes in the placement of the apparatus on the user's head. For instance, the headgear apparatus may not necessarily stay in the same position on the head of the user. The apparatus may slide down the bridge of the nose, move closer to or further away from the cornea of the eye, or tilt slightly from side to side. The algorithm may be configured to adjust or recalibrate its calculation of the eye gaze direction based on such changes.

In other examples, computer program code may be designed with the processor 322 to identify when the eye is open or shut (e.g., blinking or indefinitely closed). Based on changes in the measured capacitance at a sensor, or the overall profile of the measured capacitance, the processor may be configured to detect eye blinking or eye closure. In certain examples, the processor and associated algorithm may be configured to ignore data representing an eye blink. In other processing applications, an algorithm may be programmed to identify eye closures for greater than a defined period of time. As previously noted, this may be beneficial in a scenario where it is important to identify if a person is alert or in danger of falling asleep.

Figure 4:
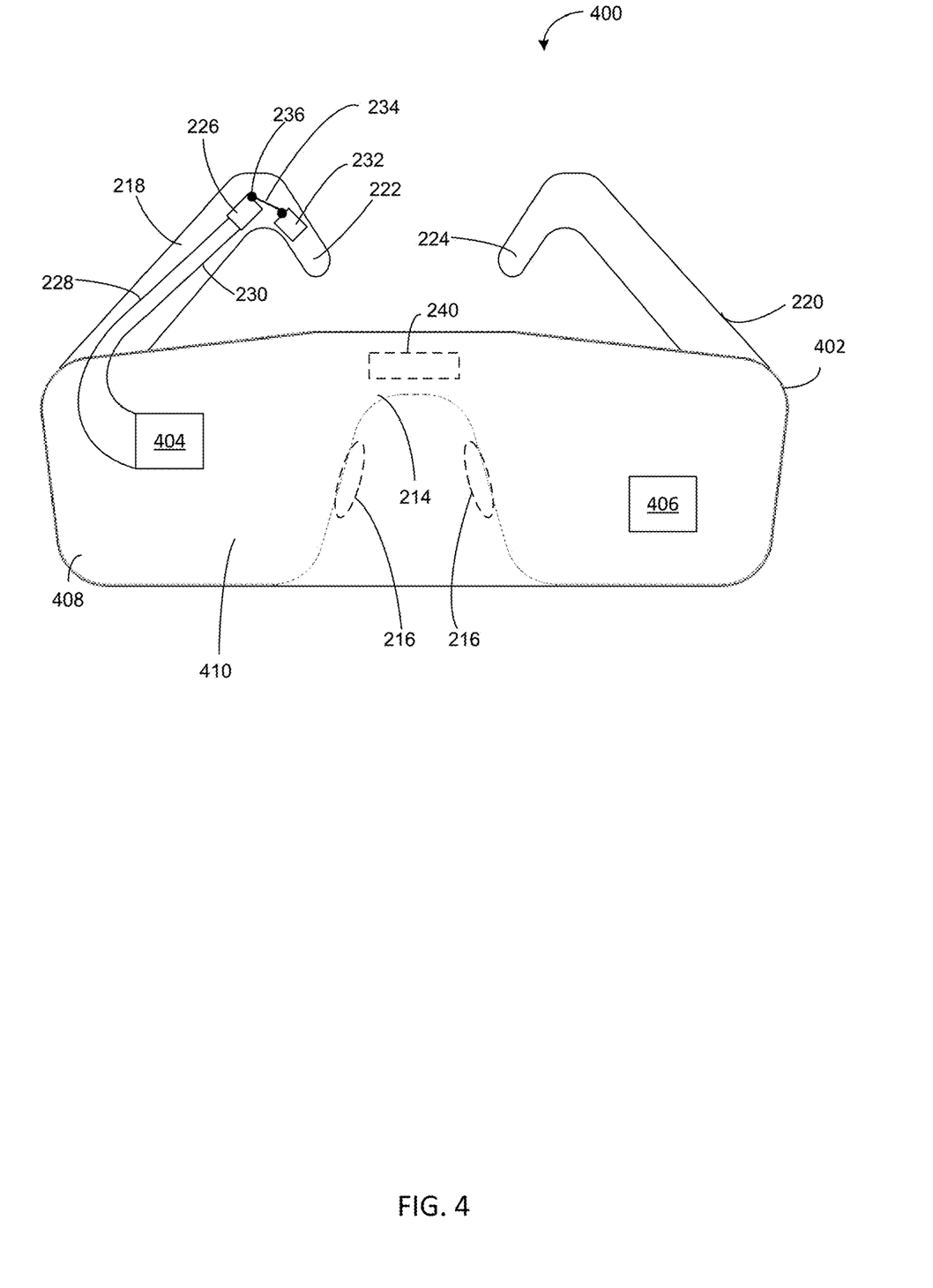
FIG. 4 depicts an additional example of a frame supporting a plurality of sensors.

FIG. 4 depicts an additional non-limiting example of an apparatus 400 having a frame 402 supporting capacitive sensors 404, 406. Similar elements discussed with FIG. 2 are depicted in FIG. 4 as well without further discussion. The frame 402 includes a frame front 408 having a single viewing area 410 for both the right and left eyes. The single viewing area 410 may be configured such that the user's peripheral vision is enclosed within the entirety of the viewing area. Such a single viewing area may be useful for an augmented reality or virtual reality application, wherein complete immersion of the user within the viewing area is desired.

Figure 5A:
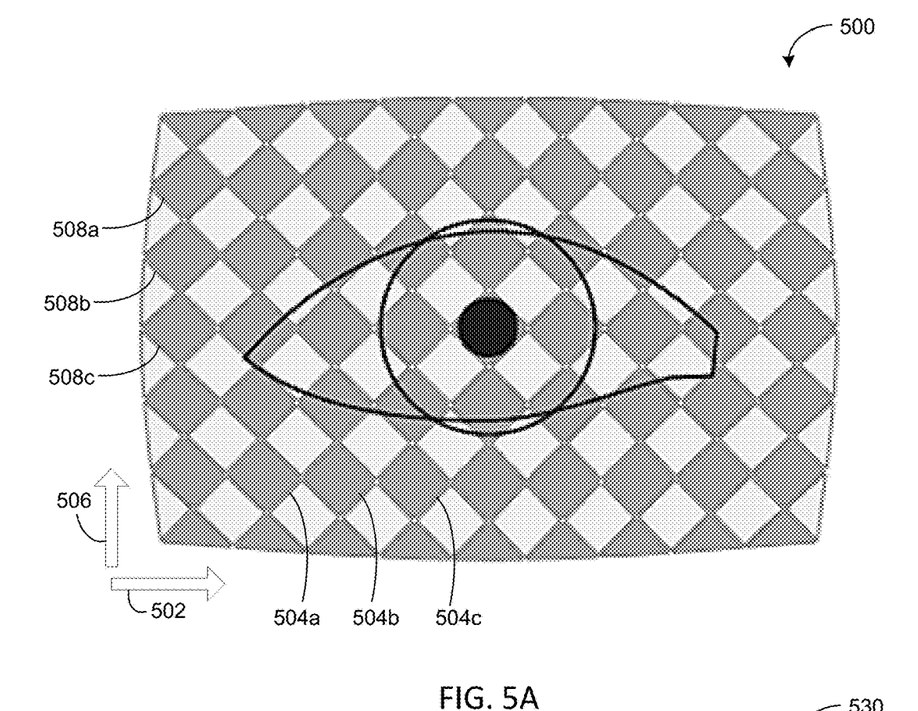
FIGS. 5A and 5B depict examples of capacitive sensor arrangements.
Figure 5B:
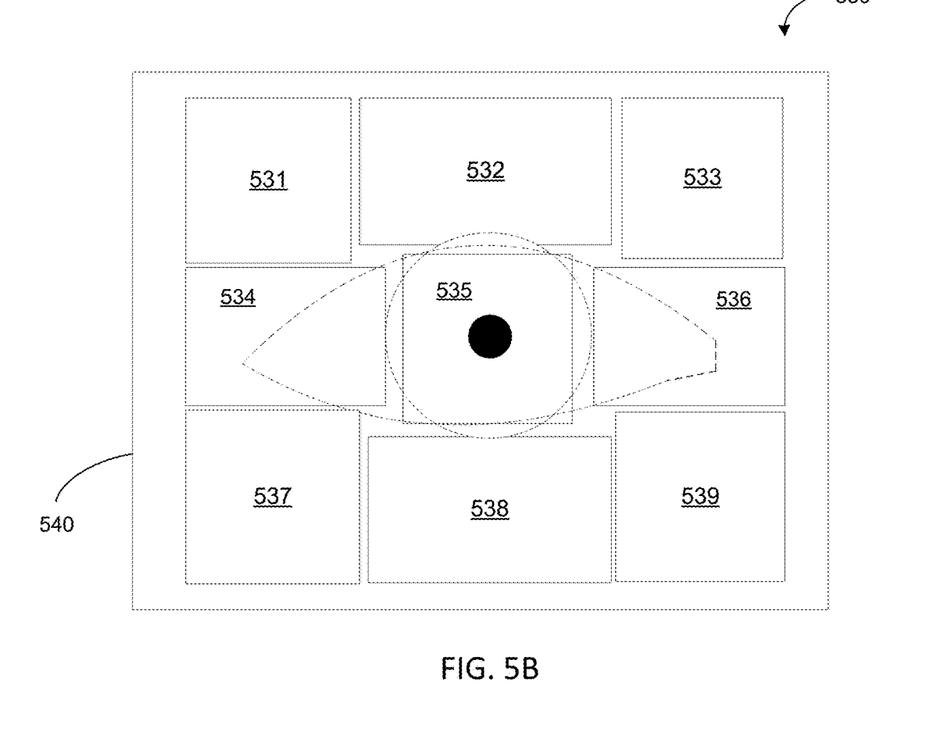

FIGS. 5A and 5B depict non-limiting examples of capacitive sensor arrangements. The type and the arrangement of the capacitive sensors are configurable. For example, the sensors may be made of transparent material or undetected material. For example, the sensors may include a set of thin wires where each wire has a width small enough such that the set of wires is not detected by the user's vision is not impaired while wearing the apparatus. The transparent capacitive sensors may be integrated or embedded within a viewing area of the apparatus, or applied to a surface of the viewing area. For example, the capacitive sensors may be affixed to a surface of the viewing area (e.g., a lens) by an optical adhesive such that the capacitive sensors reside between the eye of the user and the lens. In an alternative example, the sensors may be positioned on the opposite surface of the viewing area (e.g., lens) such that the lens is positioned between the eye of the user and the capacitive sensors.

In certain examples, the capacitive sensors may be positioned on the surface of or behind an opaque viewing frame (e.g., for virtual reality headgear or video glasses).

The capacitive sensors may be configured as self-capacitance sensors or mutual-capacitance sensors. In certain examples, the capacitive sensors may be formed of one or more sheets of conductive material (e.g., wires). One sheet may include a set of conductors (e.g., wire meshes) originating along an x-axis and a second sheet may include a set of conductors originating along a y-axis, perpendicular to the x-axis, and placed over the sheet of conductors originating from the x-axis. The conductors may be made of materials selected from a group consisting of thin metal films, inherently conductive polymers (e.g., polyacetylene, polypyrrole, polyaniline, polythiophenes, and copolymers thereof), indium tin oxide (ITO), carbon nanotubes, graphene, silver nanowires, zinc oxides (e.g., gallium zinc oxide, aluminum zinc oxide, indium zinc oxide), and combinations thereof.

A non-limiting example of a capacitive sensor arrangement 500 is depicted in FIG. 5A as a diamond pattern. The arrangement 500 includes a set of conductors originating along the x-axis 502. The arrangement 500 also includes a set of conductors originating along the y-axis 506, therein intersecting conductors from the x-axis at a perpendicular angle. Dark diamonds are connected horizontally forming rows, and light diamonds are connected vertically, forming columns, wherein the entire interior of the diamond is conductive.

Alternative arrangements are also possible. For example, a set of wires originating at the x-axis may run parallel with the y-axis, while the set of wires originating at the y-axis may run parallel with the x-axis, therein forming a square pattern between nodes. In some examples, the sets of conductors originating from the x- and y-axis may not be uniform in spacing between wires. For instance, the conductors may be spaced farther apart at locations on the periphery of the viewing area.

In other examples, the capacitive sensors may be arranged in sections or nodes. Each node may be a section of conductive material (e.g., wire mesh) separate from each additional node positioned within the viewing area in front of an eye. The number of nodes is variable. In certain examples, at least one node is positioned in front of each eye. In other examples, the number of nodes in front of each eye may be at least 2, 3, 4, 5, 6, 7, 8, 9, or 10. In certain examples, the number of nodes provided is based on the size of the viewing area (e.g., to fill the entire viewing area or a defined portion thereof).

The placement of each node in front of left eye may be coordinated with the placement of each node in front of the right eye. In certain examples, the number and position of nodes in front of the left eye is the same as to the number and position of nodes in front of the right eye. Alternatively, the position of the nodes in front of the left eye may be a mirror image of the nodes in front of the right eye.

In some examples, the number of nodes is coordinated to provide the least number of nodes possible for the two eyes. For instance, if a node is positioned up and to the left of the left eye (as viewed by the left eye), a corresponding node may not be required in the same location for the right eye. Presuming that both eyes are looking in the same direction (e.g., up and to the left), the measured capacitance in the node positioned in front of the left eye will increase. A similarly positioned node in front of the right eye would provide confirmation of the eye gaze direction, but would not necessarily be required. Therefore, in certain examples, the number of nodes positioned in front of one eye is coordinated with the nodes in front of the second eye to limit or avoid any redundancies. Nonetheless, in other examples, it may be desirable and still cost-effective to provide redundancies and confirmation of eye gaze direction. In such examples, a larger number of capacitive nodes may be positioned in front of each eye.

FIG. 5B depicts one non-limiting example of a node or conductor arrangement 530. Nine nodes/conductors 531-539 are provided within the viewing area 540 in front of an eye. The size of the nodes/conductors are variable. The placement of each node/conductor may be such that the spacing between each node is less than 1 mm. Using nine nodes/conductors, the capacitive sensors may track eye gaze in nine possible directions (e.g., up-left, up, up-right, left, center, right, down-left, down, down-right). Each node/conductor may be made from a conductive material such as a wire mesh material, as discussed above. In certain examples, each node/conductor is a self-capacitance sensor. Each node/conductor may have height and width dimensions of 1-20 mm by 1-20 mm, 10-20 mm by 10-20 mm, 1-10 mm by 1-10 mm, or 1-5 mm by 1-5 mm. In one example, the average height and width dimensions for the nodes are 10 mm by 10 mm.

The arrangement or positioning of the sensors within the viewing area of the apparatus is variable. In one example, an array of sensors may be centrally positioned in front of each eye. The array may have a defined width and height such that the array may be positioned within a large number of viewing areas. For example, there are a large number of unique eyeglass frames, and viewing areas within those frames. Therefore, having a standardized array of sensors that may be placed in each of the different frames (or at least a majority of the different frames) may simplify any eye gaze tracking algorithms associated with the sensor array. In other words, having a fixed area of sensors universal to each user may be beneficial in eliminating unnecessary calibration procedures for the apparatus and/or providing an improved tracking algorithm. In certain examples, the array of sensors may have a standardized width of 20-40 mm and a standardized height of 15-25 mm.

In other examples, the array of sensors may be customized to the viewing area. The array may cover the entire viewing area or a selected portion thereof. In some examples, the array of sensors may be positioned in an outline arrangement around the central location of each eye.

Exemplary Method for Eye Gaze Tracking

Figure 6:
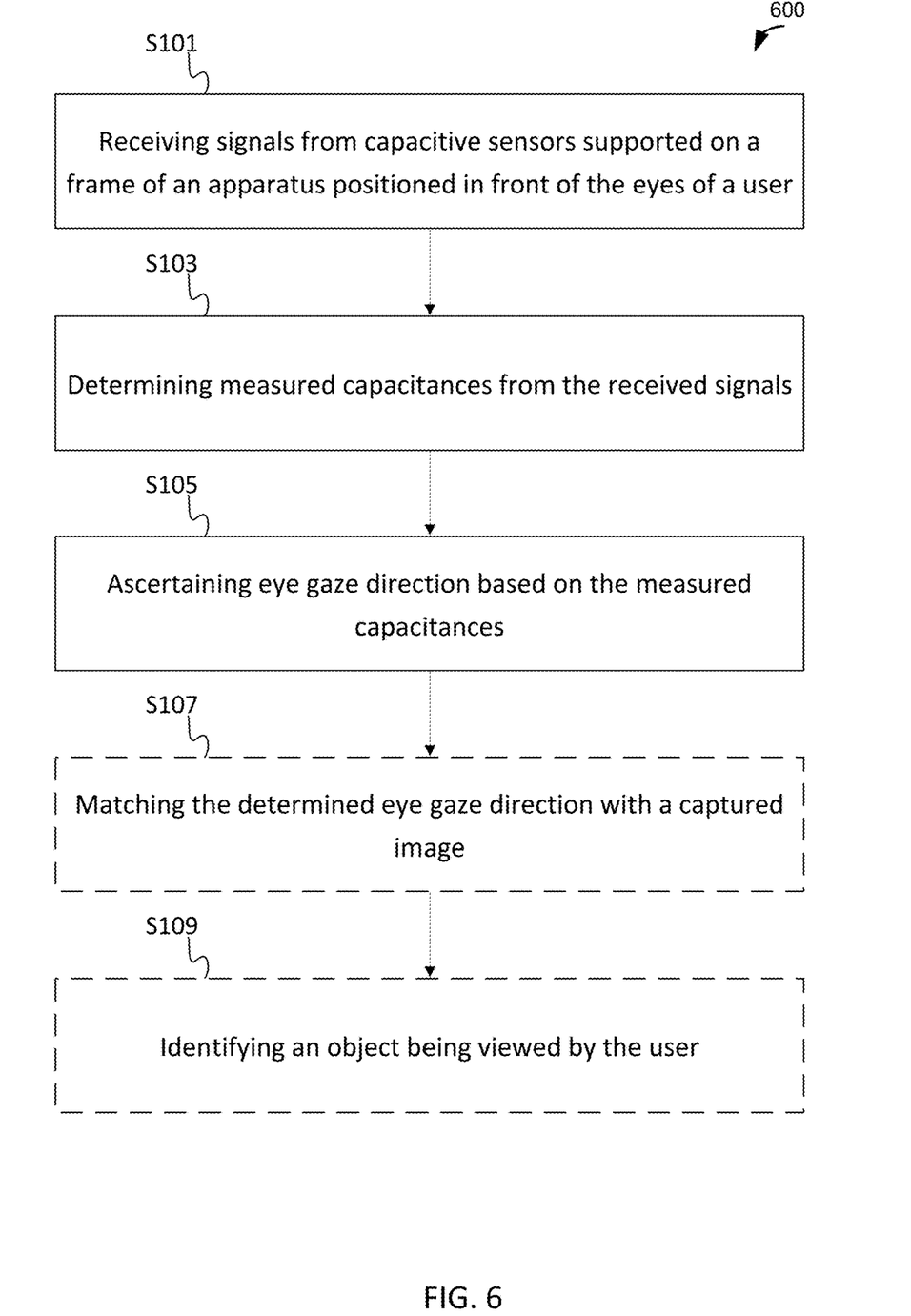
FIG. 6 is a flow diagram of a computer-implemented method of determining eye gaze using capacitive sensors in accordance with one example.

FIG. 6 depicts an exemplary method 600 for determining eye gaze direction. The method 600 is computer-implemented. For example, one or more computers of the computing environment 308 depicted in FIG. 3 and/or another electronic device may be configured to implement the method or a portion thereof. The implementation of each act may be directed by respective computer-readable instructions executed by the processor 322 (FIG. 3), and/or another processor or processing system. Additional, fewer, or alternative acts may be included in the method 600.

At act S101, the processor receives signals from the capacitive sensors supported on the frame of the headgear apparatus positioned in front of the user's eyes. The signals have been transmitted from the capacitive sensor to the control circuit or analog front-end circuit, wherein an amplifier unit may amplify the signal. The amplified signal may be sent to an ADC to convert the analog signal to a digital signal for further processing. The signals may be wirelessly or wire transmitted to the processor from the control circuit.

At act S103, the processor determines the capacitance of each received signal from the control circuit. Measured capacitances may be determined for the entire capacitive sensor array.

At act S105, the eye gaze direction is determined based at least on the measured capacitances. In certain examples, the eye gaze direction may correlate with the highest measured capacitance, as this represents the point at which a capacitive sensor is closest to the cornea of the eye of the user. In other examples, an interpolation function may be used to estimate eye gaze direction with finer resolution than provided between the pitch between sensor elements. In some examples, eye gaze direction is determined based at least on a comparison or correlation between measured capacitances of the right eye with the measured capacitances of the left eye. In such an example, it is presumed that the right eye and the left eye are looking in the same direction.

At act S107, the determined eye gaze direction may be optionally matched with an image captured by a camera. The camera is a frame of reference camera positioned on the frame of the headgear apparatus and facing away from the user.

At act S109, based at least on the matched image with the determined eye gaze direction, an object being viewed by the user may be identified.

Exemplary Computing Environment

Figure 7:
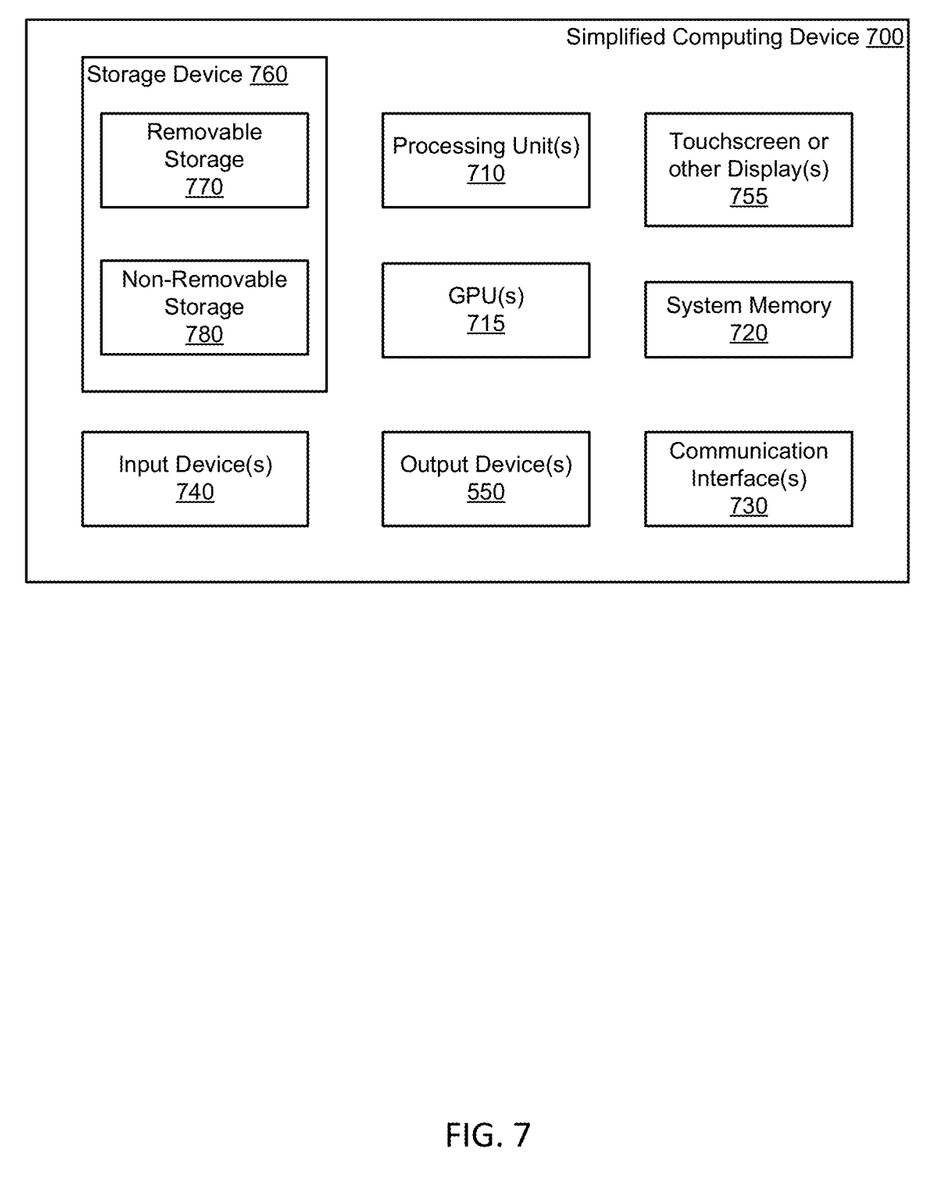
FIG. 7 is a block diagram of a computing environment in accordance with one example for implementation of the disclosed methods and systems or one or more components or aspects thereof.

With reference to FIG. 7, an exemplary computing environment 700 may be used to implement one or more aspects or elements of the above-described methods and/or systems and/or devices. The computing environment 700 may be used by, incorporated into, or correspond with, the headgear apparatus 200 (FIG. 2) or headgear apparatus 400 (FIG. 4) or one or more elements thereof. For example, the computing environment 700 may be used to implement one or more elements of the headgear apparatus.

The computing environment 700 may be a general-purpose computer system or graphics- or display-based subsystem used to implement one or more of the acts described in connection with FIG. 6. The computing environment 700 may correspond with one of a wide variety of computing devices, including, but not limited to, personal computers (PCs), server computers, tablet and other handheld computing devices, laptop or mobile computers, communications devices such as mobile phones, multiprocessor systems, microprocessor-based systems, set top boxes, programmable consumer electronics, network PCs, minicomputers, mainframe computers, or audio or video media players. In certain examples, the computing device may be a wearable electronic device, wherein the device may be worn on or attached to a person's body or clothing. The wearable device may be attached to a person's shirt or jacket; worn on a person's wrist, ankle, waist, or head; or worn over their eyes or ears. Such wearable devices may include a watch, heart-rate monitor, activity tracker, or head-mounted display.

The computing environment 700 has sufficient computational capability and system memory to enable basic computational operations. In this example, the computing environment 700 includes one or more processing unit(s) 710, which may be individually or collectively referred to herein as a processor. The computing environment 700 may also include one or more graphics processing units (GPUs) 715. The processor 710 and/or the GPU 715 may include integrated memory and/or be in communication with system memory 720. The processor 710 and/or the GPU 715 may be a specialized microprocessor, such as a digital signal processor (DSP), a very long instruction word (VLIVV) processor, or other microcontroller, or may be a general purpose central processing unit (CPU) having one or more processing cores. The processor 710, the GPU 715, the system memory 720, and/or any other components of the computing environment 700 may be packaged or otherwise integrated as a system on a chip (SoC), application-specific integrated circuit (ASIC), or other integrated circuit or system.

The computing environment 700 may also include other components, such as, for example, a communications interface 730. One or more computer input devices 740 (e.g., pointing devices, keyboards, audio input devices, video input devices, haptic input devices, or devices for receiving wired or wireless data transmissions) may be provided. The input devices 740 may include one or more touch-sensitive surfaces, such as track pads. Various output devices 750, including touchscreen or touch-sensitive display(s) 755, may also be provided. The output devices 750 may include a variety of different audio output devices, video output devices, and/or devices for transmitting wired or wireless data transmissions.

The computing environment 700 may also include a variety of computer readable media for storage of information such as computer-readable or computer-executable instructions, data structures, program modules, or other data. Computer readable media may be any available media accessible via storage devices 760 and includes both volatile and nonvolatile media, whether in removable storage 770 and/or non-removable storage 780.

Computer readable media may include computer storage media and communication media. Computer storage media may include both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may accessed by the processing units of the computing environment 700.

The eye gaze tracking techniques described herein may be implemented in computer-executable instructions, such as program modules, being executed by the computing environment 700. Program modules include routines, programs, objects, components, or data structures that perform particular tasks or implement particular abstract data types. The techniques described herein may also be practiced in distributed computing environments where tasks are performed by one or more remote processing devices, or within a cloud of one or more devices, that are linked through one or more communications networks. In a distributed computing environment, program modules may be located in both local and remote computer storage media including media storage devices.

The techniques may be implemented, in part or in whole, as hardware logic circuits or components, which may or may not include a processor. The hardware logic components may be configured as Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), and/or other hardware logic circuits.

The technology described herein is operational with numerous other general purpose or special purpose computing system environments or configurations. Examples of well-known computing systems, environments, and/or configurations that may be suitable for use with the technology herein include, but are not limited to, personal computers, hand-held or laptop devices, mobile phones or devices, multiprocessor systems, microprocessor-based systems, set top boxes, programmable consumer electronics, network PCs, minicomputers, mainframe computers, distributed computing environments that include any of the above systems or devices.

The technology herein may be described in the general context of computer-executable instructions, such as program modules, being executed by a computer. Generally, program modules include routines, programs, objects, components, data structures, and so forth that perform particular tasks or implement particular abstract data types. The technology herein may also be practiced in distributed computing environments where tasks are performed by remote processing devices that are linked through a communications network. In a distributed computing environment, program modules may be located in both local and remote computer storage media including memory storage devices.

While the present claim scope has been described with reference to specific examples, which are intended to be illustrative only and not to be limiting of the claim scope, it will be apparent to those of ordinary skill in the art that changes, additions and/or deletions may be made to the disclosed embodiments without departing from the spirit and scope of the claims.

The foregoing description is given for clearness of understanding only, and no unnecessary limitations should be understood therefrom, as modifications within the scope of the claims may be apparent to those having ordinary skill in the art.

Claim Support Section

In a first embodiment, an apparatus comprises a capacitive sensor array having a plurality of capacitive sensors, the capacitive sensor array configured to detect eye movement based at least on a proximity of the plurality of capacitive sensors to a part of an eye of a user; a frame configured to be worn on a head of the user and configured to support the capacitive sensor array positioned in front of the eye; at least one control circuit configured to receive signals from the capacitive sensor array, the control circuit positioned on or within the frame; a body electrode positioned on the frame and electrically connected to the control circuit, the body electrode configured to establish an electrical connection with a body of the user; and a conductive line connecting the body electrode to the control circuit.

In a second embodiment, with reference to the first embodiment, the frame comprises a frame front and at least one end piece extending from the frame front, the end piece configured to rest on an ear of the user, and wherein the body electrode is positioned on a temple of the end piece.

In a third embodiment, with reference to the first embodiment or the second embodiment, the frame comprises a frame front having a bridge with at least one nose pad configured to support the frame on a nose of the user, and wherein the body electrode is positioned on the nose pad.

In a fourth embodiment, with reference to any of embodiments 1-3, the plurality of capacitive sensors comprises at least one self-capacitance sensor.

In a fifth embodiment, with reference to any of embodiments 1-4, the plurality of capacitive sensors comprises at least one mutual-capacitance sensor.

In a sixth embodiment, with reference to any of embodiments 1-3, the plurality of capacitive sensors comprises self-capacitance nodes.

In a seventh embodiment, with reference to any of embodiments 1-6, the plurality of capacitive sensors comprises indium tin oxide, carbon nanotubes, graphene, zinc oxides, silver nanowires, or a metal wire mesh.

In an eighth embodiment, with reference to any of embodiments 1-7, the apparatus further comprises a camera positioned on the frame, the camera configured to capture real time images in front of the user.

In a ninth embodiment, with reference to any of embodiments 1-8, the apparatus further comprises at least one contact lens configured to be placed on a cornea of the eye of the user, wherein the contact lens comprises a conductive material configured to assist the capacitive sensory array in detecting eye movement.

In a tenth embodiment, with reference to any of embodiments 1-9, the apparatus is wirelessly connected with a computing device configured to determine eye gaze direction based at least on the signals from the capacitive sensor array.

In an eleventh embodiment, with reference to any of embodiments 1-10, the part of the eye is a bulge in a cornea of the eye.

In a twelfth embodiment, with reference to any of embodiments 1-11, the apparatus further comprises a voltage source coupled to the capacitive sensor array and coupled to the body electrode; and an amplifier coupled to the capacitive sensor array and coupled to the body electrode, wherein each capacitive sensor of the capacitive sensor array is configured to change capacitance in response to eye movement and configured to provide a signal to the amplifier in response to the change in capacitance.

In a thirteenth embodiment, an apparatus comprises at least one processor; and at least one memory including computer program code for one or more programs; the at least one memory and the computer program code configured to, with the at least one processor, cause the apparatus to at least perform: receive signals from a capacitive sensor array positioned in front of an eye of a user; determine a plurality of measured capacitances from the received signals; and ascertain an eye gaze direction of the eye of the user based at least on the plurality of measured capacitances.

In a fourteenth embodiment, with reference to the thirteenth embodiment, the eye gaze direction is determined within 10 milliseconds of receiving the signals from the capacitive sensor array.

In a fifteenth embodiment, with reference to the thirteenth embodiment or the fourteenth embodiment, the computer program code is configured to calibrate the received signals from the capacitive sensor array based at least on a shape of a frame worn on a head of a user and supporting the capacitive sensor array.

In a sixteenth embodiment, with reference to any of embodiments 13-15, the at least one memory and the computer program code are configured to cause the apparatus to further perform: calibrate the capacitive sensor array, prior to ascertaining the eye gaze direction, with the eye of the user.

In a seventeenth embodiment, with reference to any of embodiments 13-16, ascertaining the eye gaze direction comprises comparing the plurality of measured capacitances with a calibration table that correlates capacitance with direction of eye gaze.

In an eighteenth embodiment, with reference to any of embodiments 13-17, the capacitive sensor array is supported by a frame worn a head of a user; and wherein the at least one memory and the computer program code are configured to cause the apparatus to further perform: identify movement of the frame on the user's head; and adjust the eye gaze direction based on a change in location of the capacitive sensor array.

In a nineteenth embodiment, with reference to any of embodiments 13-18, the at least one memory and the computer program code are configured to cause the apparatus to further perform: identify whether the eye of the user is closed or open.

In a twentieth embodiment, a method comprises receiving, using a processor, signals from capacitive sensors supported on a frame of a headgear apparatus positioned in front of a right eye and a left eye of a user; determining measured capacitances from the received signals for the right eye and the left eye; and ascertaining eye gaze direction based at least on the measured capacitances.

In a twenty-first embodiment, with reference to the twentieth embodiment, ascertaining the eye gaze direction comprises correlating the measured capacitances of the right eye with the measured capacitances of the left eye.

In a twenty-second embodiment, with reference to the twentieth embodiment or the twenty-first embodiment, the method further comprises capturing an image with a frame of reference camera affixed to the frame of the headgear apparatus facing away from the user; matching the ascertained eye gaze direction with the image; and identifying an object being viewed by the user.

What is claimed is:

1. A wearable device comprising:
   a lens;
   a plurality of sensors positioned on a surface of the lens or within the lens, wherein each sensor of the plurality of sensors is positioned in a separate location and is electrically disconnected from each additional sensor on the surface of the lens or within the lens, and wherein the plurality of sensors is configured to detect eye movement based at least on a proximity of the plurality of sensors to a part of an eye of a user;
   a frame configured to be worn on a head of the user, wherein the frame supports the lens and the plurality of sensors; and
   a body electrode positioned on the frame to provide a grounding connection between the plurality of sensors and the user's body.

2. The wearable device of claim 1, further comprising:
a processor configured to analyze signals from the plurality of sensors to determine eye gaze direction, wherein the processor is positioned on or within the frame.

3. The wearable device of claim 2, further comprising:
a wire connecting the body electrode to the processor.

4. The wearable device of claim 3, wherein the frame comprises a frame front and at least one end piece extending from the frame front, the end piece configured to rest on an ear of the user, and
wherein the body electrode is positioned on a temple of the end piece.

5. The wearable device of claim 3, wherein the frame comprises a frame front having a bridge with at least one nose pad configured to support the frame on a nose of the user, and
wherein the body electrode is positioned on the nose pad.

6. The wearable device of claim 1, wherein the plurality of sensors comprises self-capacitance sensors.

7. The wearable device of claim 1, wherein the plurality of sensors comprises mutual-capacitance sensors.

8. The wearable device of claim 1, wherein the plurality of sensors comprises indium tin oxide, carbon nanotubes, graphene, zinc oxides, silver nanowires, or a metal wire mesh.

9. The wearable device of claim 1, further comprising:
a camera positioned on the frame, the camera configured to capture real time images in front of the user.

10. The wearable device of claim 1, wherein the wearable device is configured to wireless connect with a computing device configured to determine eye gaze direction based at least on the signals from the plurality of sensors.

11. The wearable device of claim 1, further comprising:
a voltage source coupled to the plurality of sensors and coupled to a body electrode; and
an amplifier coupled to the plurality of sensors and coupled to the body electrode,
wherein each sensor of the plurality of sensors is configured to change capacitance in response to eye movement and configured to provide a signal to the amplifier in response to the change in capacitance.

12. An apparatus comprising:
a plurality of sensors positioned on a surface of a lens or within the lens, wherein each sensor of the plurality of sensors is positioned in a separate location and is electrically disconnected from each additional sensor on the surface of the lens or within the lens;
a body electrode electrically connected to the plurality of sensors, the body electrode providing an electrical ground to the plurality of sensors; and
at least one processor configured to:
receive signals from the plurality of sensors positioned in front of an eye of a user;
determine a plurality of measured capacitances from the received signals; and
ascertain an eye gaze direction of the eye of the user based at least on the plurality of measured capacitances.

13. The apparatus of claim 12, wherein the at least one processor is configured to calibrate the received signals from the plurality of sensors based at least on a shape of a frame worn on a head of the user and supporting the lens and the plurality of sensors.

14. The apparatus of claim 12, wherein the at least one processor is further configured to calibrate the plurality of sensors, prior to ascertaining the eye gaze direction, with the eye of the user.

15. The apparatus of claim 12, wherein ascertaining the eye gaze direction comprises comparing the plurality of measured capacitances with a calibration table that correlates capacitance with direction of eye gaze.

16. The apparatus of claim 12, wherein the plurality of sensors is supported by a frame configured to be worn on a head of the user; and
wherein the at least one processor is further configured to:
identify movement of the frame on the user's head; and
adjust the eye gaze direction based on a change in location of the plurality of sensors.

17. The apparatus of claim 12, wherein the at least one processor is further configured to identify whether the eye of the user is closed or open.

18. A method comprising:
receiving, using a processor, signals from a plurality of sensors positioned on a surface of at least one lens or within the at least one lens, wherein each sensor of the plurality of sensors is positioned in a separate location and is electrically disconnected from each additional sensor on the surface of the lens or within the lens, and wherein the at least one lens is supported on a frame of a headgear apparatus positioned in front of a right eye and a left eye of a user;
grounding the plurality of sensors with a body electrode;
determining measured capacitances from the received signals for the right eye and the left eye; and
ascertaining eye gaze direction based at least on the measured capacitances.

19. The method of claim 18, wherein ascertaining the eye gaze direction comprises correlating the measured capacitances of the right eye with the measured capacitances of the left eye.

20. The method of claim 18 further comprising:
capturing an image with a frame of reference camera affixed to the frame of the headgear apparatus facing away from the user;
matching the ascertained eye gaze direction with the image; and
identifying an object being viewed by the user.

* * * * *